United States Patent [19]

Fiege et al.

[11] Patent Number: 5,650,542
[45] Date of Patent: Jul. 22, 1997

[54] PROCESS FOR THE PREPARATION OF 2-CHLORO-6-NITROPHENYL ALKYL SULPHIDES AND NOVEL 2-CHLORO-6-NITROPHENYL ALKYL SULPHIDES

[75] Inventors: Helmut Fiege; Ferdinand Hagedorn, both of Leverkusen, Germany

[73] Assignee: Bayer Aktiengesellschaft, Leverkusen, Germany

[21] Appl. No.: 554,143

[22] Filed: Nov. 6, 1995

[30] Foreign Application Priority Data

Nov. 14, 1994 [DE] Germany ............... 44 40 595.2

[51] Int. Cl.$^6$ ............... C07C 319/14; C07C 319/18
[52] U.S. Cl. ............................................. 568/44
[58] Field of Search ............................. 568/44, 45

[56] References Cited

PUBLICATIONS

J Med Chem (1987) vol. 30(3) pp. 465–473.
CASREACT 106: 102235 Ca Abst. Nippon Gakkaishi (1984) 9(1) 117–23.
English language abstract of JP 57-058-662, (1982).
J.J. D'Amico, et al., Phosphorus and Sulfur, vol. 7, pp. 143–148, (1979).
J.R. Beck, et al., J. Org. Chem., vol. 43, No. 10, pp. 2048–2052, (1978).
J.R. Beck, et al., J. Org. Chem., vol. 43, No. 10, pp. 2052–2055, (1978).
R. Specklin, et al., (Bull of Chim Soc. FR), pp. 621–626, (1951).
K.-D. Gundermann, et al., Houben–Weyl, vol. E 11, pp. 174–175, (1985).

M.F. Grundon, et al., J. Chem. Soc. (B), pp. 260–266, (1966).

*Primary Examiner*—Gary Geist
*Assistant Examiner*—Jean F. Vollano
*Attorney, Agent, or Firm*—Sprung Horn Kramer & Woods

[57] ABSTRACT

2-Chloro-6-nitrophenyl alkyl sulphides of the formula

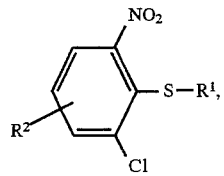
(I)

in which the substituents are as defined in the description, can be prepared by reacting 2,3-dichloro-nitrobenzenes of the formula

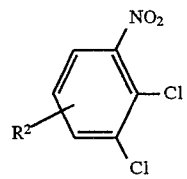
(II)

with mercaptans of the formula

HS-R$^1$ (III)

in the presence of 1–1.2 equivalents of a base per mole of mercaptan and in the presence of a phase transfer catalyst, at a temperature of 0°–100° C., in an aqueous or aqueous-organic medium. The majority of the 2-chloro-6-nitrophenyl alkyl sulphides obtainable in this way are novel.

11 Claims, No Drawings

PROCESS FOR THE PREPARATION OF 2-CHLORO-6-NITROPHENYL ALKYL SULPHIDES AND NOVEL 2-CHLORO-6-NITROPHENYL ALKYL SULPHIDES

The invention relates to a process for the preparation of 2-chloro-6-nitrophenyl alkyl sulphides by reacting the corresponding 2,3-dichloro-nitrobenzenes with mercaptans in the presence of a base and also in the presence of a phase transfer catalyst. The invention further relates to novel 2-chloro-6-nitrophenyl alkyl sulphides. Sulphides of this type are used for example for the preparation of active substances for plant protection and as intermediates for dyestuffs (Phosphorus and Sulfur 7 (1979), 143–148; Japanese patent specification 57/58662 (1982)).

It is known to convert chloronitrobenzenes containing activated chlorine atoms to the corresponding aryl methyl sulphides in alcoholic solution or suspension, in the presence of sodium hydroxide solution or potassium carbonate, by the introduction of methanethiol (Houben-Weyl, vol. E 11 (1985), p. 175). The yields achieved by this method, however, are only 52–78% of theory. The reaction of 2,3-dichloro-nitrobenzene with benzylmercaptan in the presence of a base gave 2-chloro-6-nitrophenyl benzyl sulphide in only 56% yield (Bull. 1951, 621–626).

There was a need to find a route to these compounds which was also technically suitable. It could not be ruled out here that the reducing action of the mercapto compound might cause a reaction other than the desired reaction, for example the reduction of the nitro group. Thus the formation of the corresponding aniline could be expected. Nucleophilic displacement reactions by the mercaptide also had to be expected at other substituents of the benzene ring which allow such a displacement (J. Org. Chem 43, 2048–2055 (1978)). The consequence of such secondary reactions would be the formation of by-products which might be difficult to separate off, and in any case a reduction in the yield, as is to be assumed in the case of the journal references indicated above.

The invention relates to a process for the preparation of 2-chloro-6-nitrophenyl alkyl sulphides of the formula

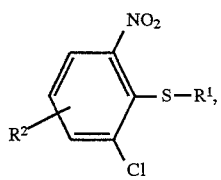

(I)

in which
R$^1$ is linear or branched C$_1$–C$_{18}$-alkyl, C$_3$–C$_8$-cycloalkyl or C$_7$–C$_{10}$-aralkyl and
R$^2$ is hydrogen, linear or branched C$_1$–C$_4$-alkyl, linear or branched C$_1$–C$_4$-alkoxy or benzyl,
which is characterized in that 2,3-dichloro-nitrobenzenes of the formula

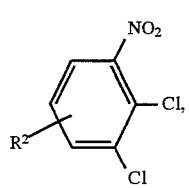

(II)

are reacted with 0.9–2 mol, preferably 1–1.5 mol, of a mercaptan of the formula

HS-R$^1$ (III), wherein
R$^1$ and R$^2$ are as defined above,
in the presence of 1–1.2 equivalents, preferably 1–1.1 equivalents, of a base per mole of mercaptan and also in the presence of a phase transfer catalyst, at a temperature of 0°–100° C., preferably 20°–80° C., in an aqueous or aqueous-organic medium.

The invention further relates to novel 2-chloro-6-nitrophenyl alkyl sulphides as defined by the formula (I), with the proviso that when R$^2$ is hydrogen, R$^1$ is not methyl, ethyl or benzyl.

Linear or branched C$_1$–C$_4$-alkyl and also C$_1$C$_{18}$-alkyl are for example methyl, ethyl, propyl, isopropyl, butyl, isobutyl, tert-butyl, the isomeric amyls, the isomeric hexyls, octyls, decyls, dodecyls, heptadecyls and octadecyls.

C$_3$–C$_8$-cycloalkyl is for example cyclopropyl, cyclobutyl, cyclopentyl, cyclohexyl, cycloheptyl, cyclooctyl, methyl-cyclopropyl, dimethyl-cyclopropyl, methyl-cyclopentyl, dimethyl-cyclopentyl, methyl- cyclohexyl or dimethyl-cyclohexyl, preferably cyclopropyl, cyclopentyl, cyclohexyl or the monomethyl or dimethyl derivatives thereof.

C$_7$–C$_{10}$-aralkyl is for example benzyl, α- or β-phenylethyl, phenylpropyl or phenylbutyl, preferably benzyl or phenyl-ethyl and particularly preferably benzyl.

Linear or branched C$_1$–C$_4$-alkoxy is for example methoxy, ethoxy, propoxy, isopropoxy, butoxy or isobutoxy.

The reaction is preferably carried out with a mercaptan of the formula

HS-R$^1$ (IV), wherein
R$^1$ is linear or branched C$_1$–C$_2$-alkyl, unsubstituted, methyl-substituted or dimethyl-substituted cyclopropyl, cyclopentyl or cyclohexyl, or C$_7$–C$_8$-aralkyl.

The reaction is particularly preferably carried out with a mercaptan of the formula

HS-R$^1$ (V), wherein
R$^1$ is linear or branched C$_1$–C$_4$-alkyl, cyclopropyl, cyclohexyl or benzyl.

A further preference is to carry out the reaction with a 2,3-dichloro-nitrobenzene of the formula

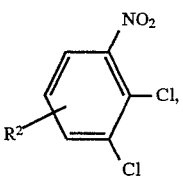

(VI)

wherein
R$^2$ is hydrogen, methyl or methoxy.

A further particular preference is to carry out the reaction with 2,3-dichloro-nitrobenzene.

Using the last-mentioned compound, the process according to the invention can be represented by the following equation:

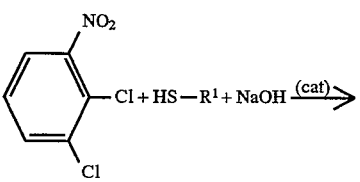

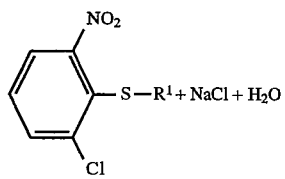

In the process according to the invention, in each case 1 mol of dichloro-nitrobenzene (II) is reacted with 0.9 to 2 mol, preferably 1 to 1.5 mol, of mercaptan (III).

Important alkylmercaptans for the process according to the invention are methylmercaptan, ethylmercaptan, isopropylmercaptan, tert-butylmercaptan, cyclohexylmercaptan and benzylmercaptan. Mercaptans are commercially available substances.

The dichloro-nitrobenzenes to be used are likewise industrially obtainable substances. Thus, for example, 2,3-dichloro-nitrobenzene is available from the nitration of o-dichlorobenzene.

The process according to the invention is carried out in the presence of 1–1.2 equivalents, preferably 1–1.1 equivalents, of a base per mole of mercaptan. Suitable bases which may be mentioned are the hydroxides and carbonates of alkali metals and alkaline earth metals. Poorly soluble or almost insoluble compounds of this type, for example alkaline earth metal carbonates, can be used in suspended form and easily participate in the reaction. Other possible bases are tertiary amines containing alkyl or benzyl groups and having a total of 3–15 C atoms. Examples of preferred bases are sodium hydroxide solution, potassium hydroxide solution, sodium carbonate, potassium carbonate, triethylamine or N,N-dimethyl-benzylamine.

Examples of suitable phase transfer catalysts are quaternary ammonium and phosphonium salts of the formulae (I) and (II):

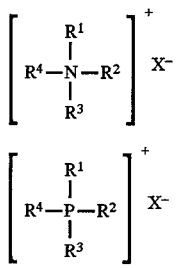

in which $R^1$ to $R^4$ are identical of different and are each a $C_1$–$C_{16}$-alkyl group which can optionally be substituted by a hydroxyl group, a $C_6$–$C_{10}$-aryl group, a $C_7$–$C_{11}$-aralkyl group or a $C_5$–$C_7$-cycloalkyl group, it also being possible for two of the radicals $R^1$ to $R^4$ together to form a ring having 5 to 7 C atoms, and X is a halogen, a bisulphate radical or a hydroxyl group.

Preferably, $R^1$ to $R^4$ are identical or different and are each methyl, ethyl, n-propyl, i-propyl, n-butyl, i-butyl, t-butyl or benzyl. X is preferably chlorine or bromine.

Particularly preferred phase transfer catalysts are tetra-n-butyl-ammonium bromide and benzyltriethylammonium chloride, which are particularly readily obtainable.

The phase transfer catalyst can be used for example in an amount of 0.001 to 0.2 mol equivalent, based on 2,3-dichloro-nitrobenzene, this amount preferably being 0.01 to 0.1 mol equivalent.

The process according to the invention is carried out in the temperature range 0°–100° C., preferably 20°–80° C. The pressure over the reaction system is not critical, so the process is preferably carried out at normal pressure. A moderately elevated working pressure is only necessary for keeping low-boiling reactants in the liquid state of aggregation, in which case a suitable pressure range is 1–8 bar, preferably 1–5 bar.

The process according to the invention can be carried out in different variants. Thus the dichloro-nitrobenzene can be introduced as a melt into an aqueous solution of an alkylmercaptide (formed by means of one of the abovementioned bases) in the simultaneous presence of a phase transfer catalyst, and the reaction can be carried out in the chosen temperature range.

Preferably, an aqueous alkylmercaptide solution is added to the dichloro-nitrobenzene melt as a suspension in water in the presence of a phase transfer catalyst.

Other embodiments of the process consist in dissolving the dichloro-nitrobenzene in an organic solvent and introducing the solution into the alkylmercaptide in the presence of the phase transfer catalyst, in the manner indicated above, or, conversely, in adding the alkylmercaptide in the form of an aqueous solution to the dichloro-nitrobenzene solution in the presence of the phase transfer catalyst.

Suitable solvents for the dichloro-nitrobenzene are a $C_1$–$C_6$ alkanol, a $C_3$–$C_6$ ketone, a $C_6$–$C_{12}$ (cyclo)aliphatic or aromatic hydrocarbon, a $C_1$–$C_8$ (cyclo)aliphatic or aromatic halogeno-hydrocarbon or open-chain or cyclic peralkyl-carboxamides having 3–8 C atoms. Preferred and technically important solvents are: methanol, ethanol, i-propanol, acetone, methylene chloride, chlorobenzene, toluene, xylene, dimethylformamide or N-methyl-pyrrolidone.

Another variant is to introduce a melt or a solution of the dichloro-nitrobenzene in one of said solvents into the alkylmercaptide in the presence of the phase transfer catalyst. Of these possibilities, working with a melt of the dichloro-nitrobenzene is particularly preferred because in this case an organic solvent, which has to be recycled, can be dispensed with and the process can be carried out in water only, which has the advantage of dispensing with the safety precautions associated with occupational hygiene.

Because of the susceptibility of mercaptans to oxidation by air and other oxidizing agents, it is expedient initially to react the mercaptan with a base under an inert gas, the mercapto compound being introduced under the surface of the solution or suspension of the base, especially if the mercaptans are gaseous or low-boiling.

The chloro-nitrophenyl alkyl sulphides prepared according to the invention are obtained in the reaction as water-insoluble substances. At temperatures above their melting point, such compounds can be separated from the aqueous salt solution as a melt and the salts can be extracted by stirring with hot water. After extraction by stirring with hot water to remove salts (e.g. sodium chloride), the crude sulphide can be introduced for example into a heated alcohol/water mixture and crystallized by cooling. After this recrystallization process, the product in question already has a purity of more than 99% in many cases. These high purities, combined with high selectivities in respect of the desired product, are surprising inasmuch as, in the presence of a relatively large amount of mercaptide, the nitro substituent and the adjacent chlorine atom would have been expected to undergo an exchange to form a second sulphide group. Our own experiments were able to show that such a process is to be expected in principle.

It should also be taken into account here that, in the preferred variant of the process according to the invention, where (II) is added to (III), there is a large excess of (III) relative to (II) at the beginning of the reaction. Furthermore, the reduction of the nitro group in 4-chloronitrobenzene by methylthiol to give 4,4'-dichloro-azoxybenzene and ultimately 4-chloro-aniline is known from J. Soc. Chem. Ind. 1927, 435 T.

The chlorophenyl alkyl sulphides which can be prepared according to the invention are valuable intermediates for the preparation of dyestuffs and especially active substances, for example in the plant protection sector. Examples which may be mentioned are 2-chloro-6-nitrophenyl methyl sulphide, 2-chloro-6-nitrophenyl ethyl sulphide, 2-chloro-6-nitrophenyl isopropyl sulphide, 2-chloro-6-nitrophenyl benzyl sulphide and 2-chloro-6-nitrophenyl cyclohexyl sulphide.

EXAMPLES

Example 1

40.8 g (0.525 mol) of 98% pure isopropylmercaptan were added dropwise through an immersed tube over 30 min at $-3°$ to $0°$ C., with stirring, to a solution prepared from 21.4 g (0.525 mol) of sodium hydroxide and 150 ml of water. After the addition of 2.5 g of tetrabutylammonium bromide, the mercaptide solution was heated to 65° C. and 97.0 g of molten 99.4% pure 2,3-dichloro-nitrobenzene (0.5 mol) were added dropwise over 45 min at this temperature. The mixture was subsequently stirred for 4 h at 65° C. The supernatant aqueous salt solution was neutralized with a little aqueous hydrochloric acid and separated from the product phase. The latter was then stirred with hot water, the phases were separated and the liquid product (115.5 g, 97.6% pure=97.4% of the theoretical yield) was dissolved in a hot solution of isopropanol/water, from which the product separated out as beige-coloured crystals on cooling.

Purity: 99.4% (GC), m.p. 65°–66° C.

Example 2

A solution of 42.7 g (0.55 mol) of isopropylmercaptan in aqueous sodium hydroxide solution, prepared from 22.5 g (0.5625 mol) of sodium hydroxide and 150 ml of water, was introduced over 60 min at 60° C. into a solution of 97.0 g of 2,3-dichloro-nitrobenzene (0.5 mol) in 150 ml of methanol. The mixture was subsequently stirred for 4 h at 60° C. After neutralization, the solvent was then distilled off, the product was separated from the aqueous salt solution and washed with hot water and the crude product was isolated by suction filtration. After drying, the product was obtained with a crude yield of 118.6 g. The purity by GC analysis was 96.3%. Yield: 98.6% of theory. Recrystallization from isopropanol/water gave a 99.4% pure substance.

Example 3

A solution of 40.8 g (0.52 mol) of isopropylmercaptan in aqueous sodium hydroxide solution, prepared from 21.4 g (0.535 mol) of sodium hydroxide and 150 ml of water, was added dropwise over 55 min at 60° C. to a solution of 97.0 g of 2,3-dichloro-nitrobenzene (0.5 mol) and 2.5 g of tetrabutylammonium bromide in 150 ml of toluene. The mixture was subsequently stirred for 2 h at 60° C. The solvent was then steam-distilled, the product was separated from the aqueous salt solution, washed with hot water and separated from the water and a 97.1% pure product (GC) was isolated after drying. Yield: 118 g=97% of theory.

Example 4

40.8 g (0.525 mol) of 98% pure isopropylmercaptan were added dropwise through an immersed tube over 30 min at $-3°$ C., with stirring, to a sodium hydroxide solution prepared from 21.4 g (0.525 mol) of sodium hydroxide and 150 ml of water. The resulting sodium isopropylmercaptide solution was charged into a dropping funnel and added dropwise over 55 min, with stirring, to a suspension of 97.0 g (0.5 mol) of molten 2,3-dichloro-nitrobenzene and 2.5 g of tetrabutylammonium bromide in 100 ml of water, heated to 60° to 65° C. The mixture was subsequently stirred for 3 h at 60° C. After cooling to room temperature, the crystalline product was filtered off with suction, washed with water and dried to give 117.3 g of a 98.2% pure (GC) crystalline crude substance, corresponding to a yield of 99.4% of theory. A 99.5% pure (GC) product, m.p. 66° C., was isolated after recrystallization from isopropanol/water.

Example 5

10.7 g of sodium hydroxide (0.263 mol) were dissolved in 75 ml of water in a 250 ml stirred flask. 32.9 g=39.1 ml (0.263 mol) of benzylmercaptan (99% pure) were added dropwise to this solution at 10° C., with stirring. The resulting solution was added dropwise over 40 min at 60° C., with stirring, to a suspension of 48.5 g (0.25 mol) of 2,3-dichloro-nitrobenzene (99.4% pure) and 1.3 g of tetra-n-butylammonium bromide in 50 ml of water and the mixture was subsequently stirred for 4 hours. After cooling, the crystalline product was filtered off with suction, washed with water and dried. Crude yield: 72.7 g (theory: 69.9 g, pure), m.p. 66°–68° C.

GC analysis: 93.9% of 2-chloro-6-nitrophenyl thiobenzyl ether, 4.6% of 2,3-bis-(benzylmercapto)-chlorobenzene.

Example 6

In a 250 ml stirred flask, a solution of 10.7 g (0.263 mol) of sodium hydroxide in 75 ml of water was cooled to 10° C. and 31.5 g (0.263 mol) of cyclohexylmercaptan (97% pure) were added dropwise from a dropping funnel, with stirring. The resulting emulsion (a small proportion remained undissolved) was added dropwise over 40 main at 60° C., with vigorous stirring, to a suspension of 48.5 g (0.25 mol) of 2,3-dichloro-nitrobenzene (99.4% pure) and 1.3 g of tetra-n-butylammonium bromide in 50 ml of water. The mixture was subsequently stirred for 4 hours at 60° C., cooled and filtered with suction and the crystalline product was washed with water and dried. Yield: 68.8 g, crude (theory: 67.9 g, pure), 97.8% pure by GC analysis. M.p. 74°–76° C.

Comparative Example (Displacement of $NO_2$)

A sodium benzylmercaptide solution was prepared by dissolving 20.4 g of 98% pure sodium hydroxide (0.5 mol) in 175 ml of water and adding 62.6 g (0.5 mol) of benzylmercaptan (99% pure) dropwise. This solution was added dropwise over one hour at 60° C., with vigorous stirring, to a suspension of 58.5 g (0.25 mol) of 2,3-dichloro-nitrobenzene (99.4% pure) and 1.3 g of tetrabutylammonium bromide in 50 ml of water. The progress of the reaction was observed by GC analyses of samples of the reaction mixture at 4-hour intervals:

After 4 hours at 60° C.: 37.4% of 2-chloro-6-nitrophenyl thiobenzyl ether (monosubstituted product) and 51.4% of 2,3-bis-(benzylmercapto)-chlorobenzene (disubstituted product).

After a further 4 hours at 70° C.: 21.1% of monosubstituted product and 65.3% of disubstituted product.

After a further 4 hours at 80° C.: 12.7% of monosubstituted product and 72.0% of disubstituted product.

The reaction mixture was cooled, extracted with 250 ml of toluene and concentrated. Residue: 92 g. A 92.7% pure substance (2% of monosubstituted product) was obtained by recrystallization from methanol. A 97.6% pure product of m.p. 86°–88° C. was obtained by further recrystallization from methanol.

What is claimed is:

1. A process for the preparation of a 2-chloro-6-nitrophenyl alkyl sulphide of the formula

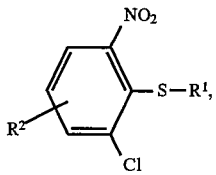

in which
R$^1$ is linear or branched C$_1$–C$_{18}$-alkyl, C$_3$–C$_8$-cycloalkyl or C$_7$–C$_{10}$-aralkyl and
R$^2$ is hydrogen, linear or branched C$_1$–C$_4$-alkyl, linear or branched C$_1$–C$_4$-alkoxy or benzyl,
in which a 2,3-dichloro-nitrobenzene of the formula

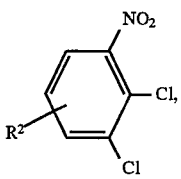

is reacted with 0.9–2 mol. of a mercaptan of the formula

HS-R$^1$, wherein
R$^1$ and R$^2$ are as defined above,
in the presence of 1–1.2 equivalents of a base per mole of mercaptan and in the presence of a phase transfer catalyst, at a temperature of 0°–100° C., in an aqueous or aqueous-organic medium.

2. The process of claim 1, in which a mercaptan of the formula

HS-R$^1$, is used, wherein
R$^1$ is linear or branched C$_1$–C$_{12}$-alkyl, unsubstituted, methyl-substituted or dimethyl-substituted cyclopropyl, cyclopentyl or cyclohexyl, or C$_7$–C$_8$-aralkyl.

3. The process of claim 1, in which a 2,3-dichloro-nitrobenzene of the formula

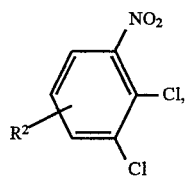

is used, wherein
R$^2$ is hydrogen, methyl or methoxy.

4. The process of claim 1, in which the mercaptan is of the formula

HS-R$^1$, wherein
R$^1$ in linear or branched C$_1$–C$_4$-alkyl, cyclopropyl, cyclohexyl or benzyl.

5. The process of claim 1, in which 2,3-dichloro-nitrobenzene is used.

6. The process of claim 1, in which a melt of the dichloro-nitrobenzene is introduced into an aqueous solution of an alkylmercaptide and a phase transfer catalyst.

7. The process of claim 1, in which an aqueous alkylmercaptide solution is added to molten dichloro-nitrobenzene as a suspension in water in the presence of a phase transfer catalyst.

8. The process of claim 1, in which the dichloronitrobenzene is used as a solution in a C$_1$–C$_6$-alkanol, C$_3$–C$_6$-ketone, C$_6$–C$_{12}$-(cyclo)aliphatic or aromatic hydrocarbon, C$_1$–C$_8$-(cyclo)aliphatic or aromatic halogenohydrocarbon or open-chain or cyclic peralkylcarboxamide having 3 to 8 C atoms.

9. The process of claim 1, in which the dichloronitrobenzene is used as a solution in methanol, ethanol, i-propanol, acetone, methylene chloride, chlorobenzene, toluene, xylene, dimethylformamide or N-methylpyrrolidone.

10. The process of claim 1, in which the phase transfer catalyst used is tetrabutylammonium bromide or benzyltrimethylammonium chloride.

11. 2-Chloro-6-nitrophenyl alkyl sulphides of the formula

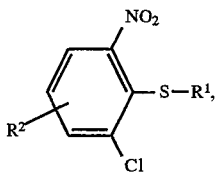

in which
R$^1$ is linear or branched C$_1$–C$_{18}$-alkyl, C$_3$–C$_8$-cycloalkyl or C$_7$–C$_{10}$-aralkyl and
R$_2$ is hydrogen, linear or branched C$_1$–C$_4$-alkyl, linear or branched C$_1$–C$_4$-alkoxy or benzyl,
R$^1$ not being methyl, ethyl or benzyl when R$^2$ is hydrogen.

* * * * *